United States Patent [19]
Olerud

[11] Patent Number: 6,027,533
[45] Date of Patent: Feb. 22, 2000

[54] DEVICE FOR FIXATING AND ADJUSTING THE POSITIONS OF VERTEBRAE IN VERTEBRAL SURGICAL OPERATIONS

[76] Inventor: Sven Olerud, Villa Malmen, S-740 11 Länna, Sweden

[21] Appl. No.: 08/913,996

[22] PCT Filed: Mar. 18, 1996

[86] PCT No.: PCT/SE96/00340

§ 371 Date: Jan. 12, 1998

§ 102(e) Date: Jan. 12, 1998

[87] PCT Pub. No.: WO96/32070

PCT Pub. Date: Oct. 17, 1996

[30] Foreign Application Priority Data

Apr. 10, 1995 [SE] Sweden ................................ 9501328

[51] Int. Cl.⁷ ................................ A61F 5/00; A61F 5/01; A61F 5/04; A61B 17/58
[52] U.S. Cl. ................................ 623/17; 606/60; 606/61; 606/62; 606/63; 606/64
[58] Field of Search ................................ 606/60, 61, 62, 606/63, 64; 623/17

[56] References Cited

U.S. PATENT DOCUMENTS 5,092,867   3/1992   Harms et al. ............................ 623/17
5,368,594   11/1994  Martin et al. ............................ 623/17

FOREIGN PATENT DOCUMENTS 0330881   9/1989   European Pat. Off. .
WO94/15554   7/1994   WIPO .

*Primary Examiner*—Mickey Yu
*Assistant Examiner*—Choon P. Koh
*Attorney, Agent, or Firm*—Finnegan, Henderson, Farabow, Garrett & Dunner, L.L.P.

[57] ABSTRACT

The present invention relates to a device for fixating and adjusting the position of vertebrae in conjunction with vertebral surgical operations, comprising two mutually crossing and generally rod-shaped implant elements. For the purpose of locking the implant elements together, the device (1) further comprises four generally parallel, elongated elements (B, C, D, E) projected onto a plane that passes through two of the elements whose ends are generally located in the corners of a parallelogram, preferably a square. The ends of the elements are mutually joined together in pairs by mutually parallel part-hoops (7, 9; 8, 10) which curve outwards from the ends of the elongated elements, wherein the pair of part-hoops (7, 9) at one end of an elongated element are perpendicular to the pair of part-hoops (8, 10) at the other end thereof, wherein the part-hoops of each said pair embrace a rod-shaped implant element (5, 6, 11a, 17) together with a respective adjacent, crossing rod-shaped element, wherein those sides (13, 14, 13', 14'; 15, 16, 15', 16') of the elongated elements that lie against a rod-shaped element are essentially flat and essentially parallel with respective opposing sides of an adjacent elongated element in fixating and positionally adjusting a vertebra.

15 Claims, 3 Drawing Sheets

6,027,533

DEVICE FOR FIXATING AND ADJUSTING THE POSITIONS OF VERTEBRAE IN VERTEBRAL SURGICAL OPERATIONS

FIELD OF INVENTION

The present invention relates to a device intended for fixating and adjusting the positions of vertebrae in vertebral or spinal surgical operations and including two mutually crossing and generally rod-shaped implant elements.

DESCRIPTION OF THE BACKGROUND ART

Many different solutions concerned with locking and fixating two generally rod-shaped implant elements placed one on the other such as to correct and stabilize adjacent vertebra have been proposed in the art. The devices used to this end are often bulky and can cause the patient considerable discomfort. These known devices are often difficult to apply and have a complicated and relatively often illogical design, making handling of the devices difficult.

BRIEF DESCRIPTION OF THE INVENTIVE CONCEPT

The object of the present invention is to eliminate the aforesaid drawbacks of known devices for locking and fixating generally rod-shaped implants, and to provide a device which can be readily manipulated quickly and smoothly and which will bind together two mutually crossing implant elements with no mechanical strength impairment.

This object is achieved in accordance with the invention by means of an implant element locking device which includes four generally parallel and elongated elements projected on a plane through two of the elements whose ends are located essentially in the corners of a parallelogram, preferably a square, wherein the ends of said elements are mutually connected in pairs by means of mutually parallel curved members which arch outwardly from the ends of the elongated elements, wherein the pair of curved members at one end of the elongated elements are perpendicular to the pair of curved members at the other end thereof, wherein each pair of curved members embraces a rod-shaped implant element together with respective adjacent mutually crossing rod-shaped elements, and wherein those sides of the elongated elements that lie against a rod-shaped element are essentially flat and essentially parallel with respective opposing sides of an adjacent elongated element for fixating and adjusting the position of vertebrae.

DETAILED DESCRIPTION OF A PREFERRED EMBODIMENT OF THE INVENTION

Figure 1:
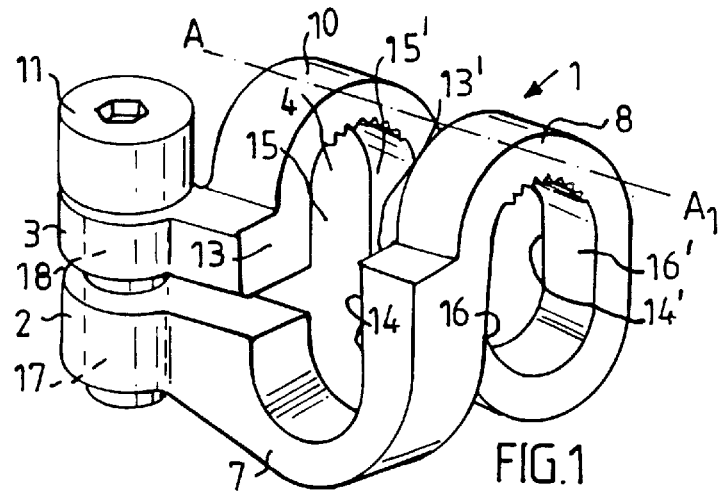
FIG. 1 is a perspective view of one embodiment of an inventive device.
Figure 2:
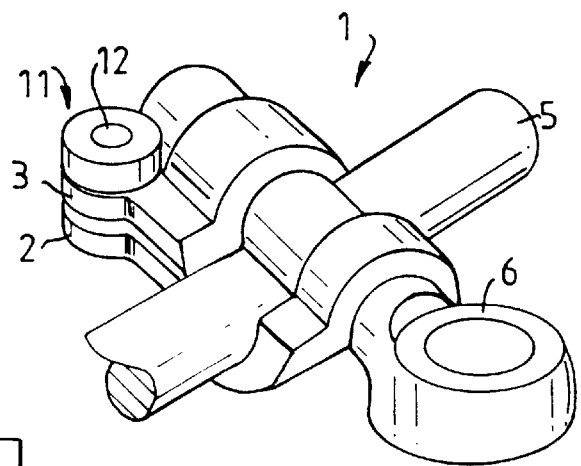
FIG. 2 shows the device of FIG. 1 with two mutually crossing rod-shaped implant elements in a locked and fixated state.
Figure 3:
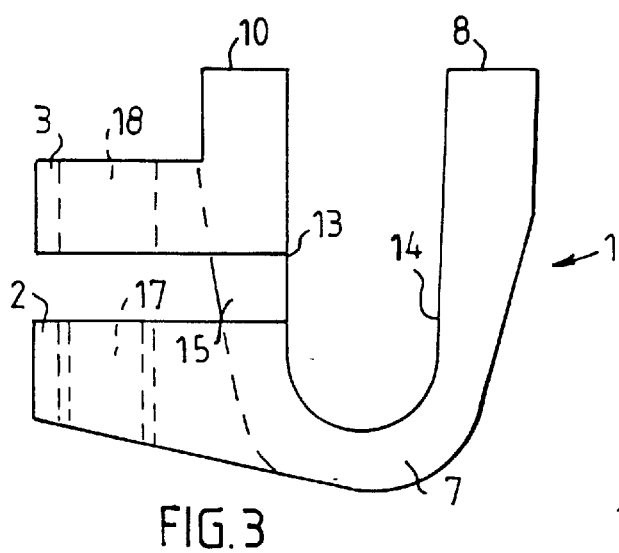
FIG. 3 is a side view of the device shown in FIG. 1.
Figure 4:
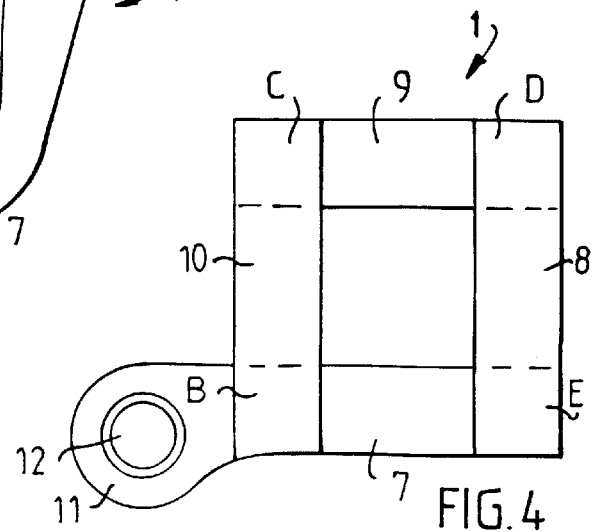
FIG. 4 shows the device of FIG. 1 from above.
Figure 5:
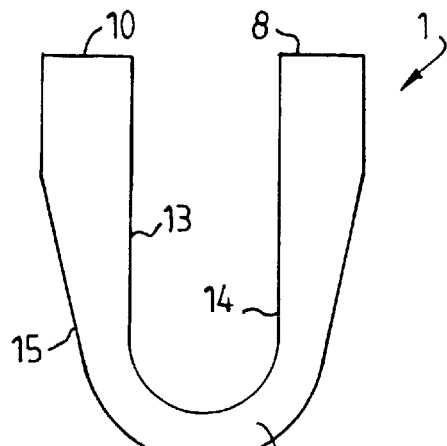
FIG. 5 is a side view of another embodiment of the inventive device.
Figure 6:
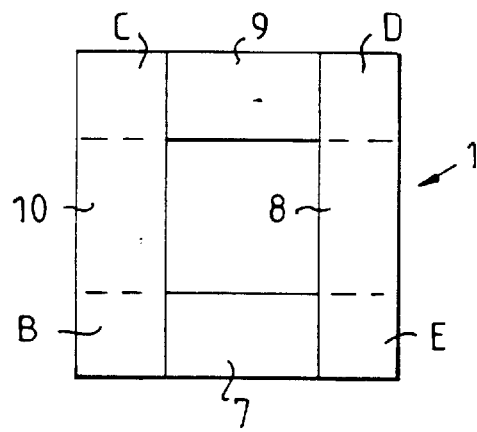
FIG. 6 shows the device of FIG. 5 from above.
Figure 7:
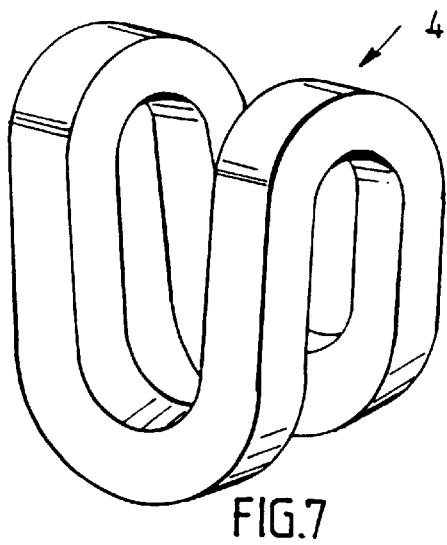
FIG. 7 is a perspective view of the device shown in FIG. 5.
Figure 8:
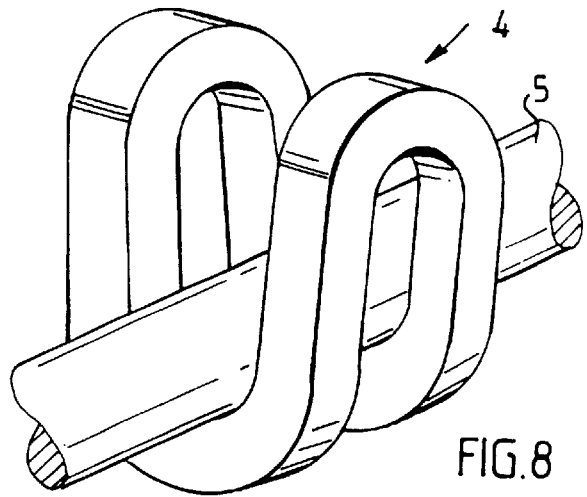
FIG. 8 shows the device of FIG. 5 with a first rod-shaped implant placed in the bottom of the device.

FIGS. 1 through 4 illustrates the main components of one embodiment of an inventive device. As will be seen from these Figures, the device comprises an elongated locking member 1 having two free ends 2, 3 and including a so-called hooped holding and clasping part 4 which embraces the rod-shaped implant elements 5, 6 and which from an initially flat state is curved about a centre line A—A through an angle of 180°, so as to form two bottom part-hoops 7, 9 and two top part-hoops 8, 10 which pair-wise embrace the rod-shaped implant elements 5, 6, wherein the free ends 2, 3-of the locking member include the hooped holding and clasping part 4 and are provided with locking and displacement means 11 which enable respective free ends to be displaced relative to one another and locked in their set positions. Each of the free ends 2, 3 includes a flange which extends out from the hooped holding and clasping part 4 essentially at right angles thereto, said flanges each having a screw-threaded hole 17, 18 which receives a screw 12. With the screw 12 loosely tightened, the mutually crossing implant rods 5, 6 disposed in the locking device 1 can be moved relative to one another when adjusting the positions of the rods 5, 6 in relation to one another and in relation to the vertebrae. When the screw 12 is fully tightened, the two rods 5 and 6 will be locked against further movement, because the space in the locking device that accommodates the rods will decrease in size in response to the reduction in distance between the two free ends 2, 3 as they are moved together, and the elongated elements are bent slightly towards one another when locking the displacing and locking means 11, thereby locking the rod-shaped implant elements 5, 6 together. The locking device 1 thus provides a double grip on each of the mutually crossing rod elements 5, 6, with the rods 5, 6 being embraced around roughly half their circumference by the arcuate part-hoops 7, 9; 8, 10 of the hooped holding and clasping part 4, with the generally parallel and planar side surfaces 13, 14, 13', 14'; 15, 16, 15', 16' facing towards and lying in abutment with said rod-shaped implants.

As the screw 12 is tightened in the locking and displacing means 11, the vertical side surfaces 13, 14, 13', 14'; 15, 16, 15', 16' will bend slightly towards one another and therewith lock the rod-shaped implant elements 5, 6 together. One of the elongated elements E, located nearest the divided element, is stiffer than the remaining elements, such that remaining elements will be rotated or twisted slightly as the ends 2, 3 are displaced relative to one another and therewith further lock the rod-shaped implant elements 5, 6.

The part-hoops 7, 8, 9, 10 are provided with serrations or friction-promoting coatings on those sides thereof that face towards the implant elements.

The locking device 1 can also be described in the following way: The device 1 includes four generally parallel and elongated elements B, C, D, E whose ends projected onto a plane that passes generally through two of the elements are located in the corners of a parallelogram, preferably a square, wherein respective ends of said elements are mutually connected in pairs by part-hoops 7, 9; 8, 10 which curve outwardly from the ends of the elongated elements, wherein the pair of part-hoops at one end of the elongated elements are perpendicular to the pair of part-hoops 8, 10 at the other end of said elements, wherein the part-hoops 7, 9, 8, 10 of each pair partially embrace a respective rod-shaped implant element 5, 6, and wherein those sides 13, 14, 13', 14'; 15, 16, 15', 16' of the elongated elements that lie in abutment with a rod-shaped element are essentially flat and generally parallel with respective opposing side of an adjacent elongated element, and wherein an elongated element is divided midway so as to form two free ends 2, 3, and wherein said free ends 2, 3 can be displaced relative to one another by means of a displacing and locking means 11. Each of the free ends 2, 3 is provided with a flange that extends outward from the hooped holding and clasping part 4 essentially at right angles thereto, and each flange has a screwthreaded hole 17, 18 into which a screw 12 is screwed. When the screw 12 is loosely tightened, the mutually crossing implant rods 5, 6 in the locking device 1 can be moved in relation to one another and twisted around their own axes to adjust the positions of the rods 5, 6 in relation to one another and in relation to the vertebrae. When the screw 12 is fully tightened, the two rods 5 and 6 will be unable to move because the size of the rod accommodating space in the device is decreased by virtue of the reduction in distance between the two free ends 2, 3 that occurs when these ends move towards one another, while the elongated elements bend slightly towards one another when locking said displacing and locking means 11, therewith to lock the rod-shaped implant elements 5, 6 together. The locking device 1 thus provides a double grip on each of the mutually crossing rod elements 5, 6, since the part-hoops 7, 9; 8, 10 embrace the rods 5, 6 around essentially half the circumference thereof and the generally parallel, flat side surfaces 13, 14, 13', 14'; 15, 16, 15', 16' face towards and lie in abutment with respective rods.

FIGS. 5–10 illustrate another embodiment of the invention. As evident from the Figures, the device includes an elongated locking device 1 which corresponds substantially to the device 1 of the embodiment illustrated in FIGS. 1–4 but has the form of a closed hoop. The holding and clasping hoop 4 functions to embrace the rod-shaped implant element 5 and a device-locking bone screw 11a that can be screwed into the vertebrae, and is curved around a centre line A—A through 180° from a flat initial state so as to form two semi-circular bottom part-hoops 7, 9 and two top part-hoops 8, 10 which pair-wise partially embrace the rod-shaped implant element 5 and the bone screw 11a. The bone screw 11a is hollow and slotted at its upper end, preferably with six slots. Screwed into the hollow is a screw having a screwthreaded cylindrical part which merges with a conical part which, in turn, merges with a cylindrical end-part by the means of which the rod implant is affixed when tightening the screw located in the upper end of the bone screw. With the screw inserted in the bone screw and loosely tightened, the mutually crossing parts disposed in the locking device 1 can be displaced in relation to one another and rotated about their own axes for adjusting the positions of the rod 5 and the bone screw 11a in relation to one another and in relation to the vertebrae. Tightening of the conical screw will lock the rod 5 and the bone screw 11a against all movement, since the accommodating space in the device decreases in size and results in an extension of the four parts of the device that extend between the rod and the bone screw. The locking device 1 thus provides a double grip around each of the mutually crossing elements 5, 11a, with the part-hoops 7, 9; 8, 10 embracing the elements 5, 11a around essentially half their circumferences and with the generally parallel, flat side surfaces 13, 14, 13', 14'; 15, 16, 15', 16' facing towards respective elements lying in abutment therewith.

Figure 9:
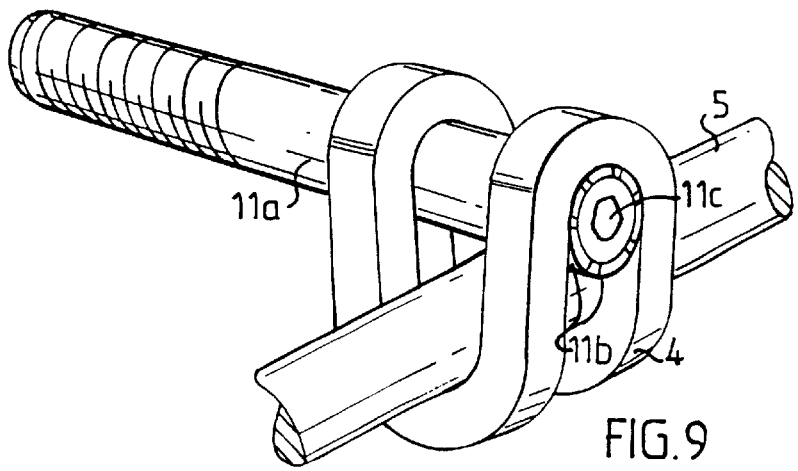
FIG. 9 shows the device of FIG. 8 with a second implant in the form of a bone screw placed at an angle of essentially 90° to the rod-shaped first implant, and comprising a further embodiment of the implant locking device.
Figure 9A:
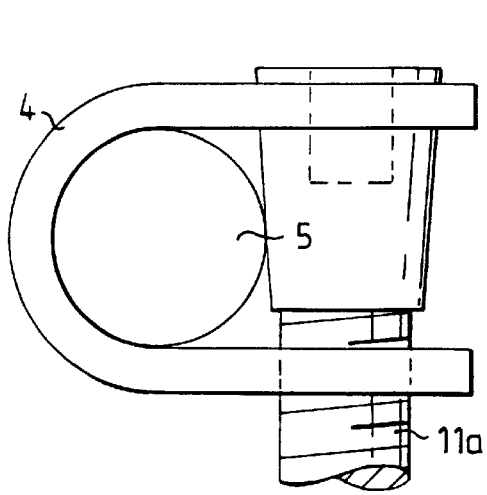
FIG. 9a shows the device of FIG. 8 with a second implant in the form of a bone screw placed at an angle of generally 90° to the rod-shaped first implant and comprising a second embodiment of the implant locking device.
Figure 10:
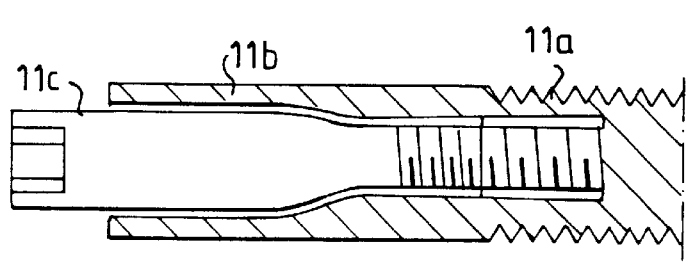
FIG. 10 is a schematic sectional view of a slotted bone screw with a conical screw lying therein.
Figure 12:
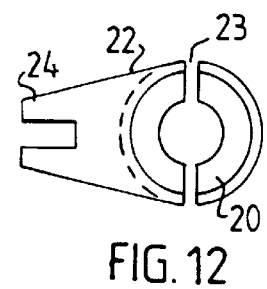
FIG. 12 shows the implant of FIG. 11 from the short end.

FIG. 9a illustrates another embodiment of the locking device in which the upper part 18a of the bone screw has an outer conical shape for locking the implant in the hooped part 4. As the bone screw is tightened, the conical part of the screw will successively reduce the accommodating space in the device and thus fixate and lock the implant in the hoop part 4.

Figure 11A:
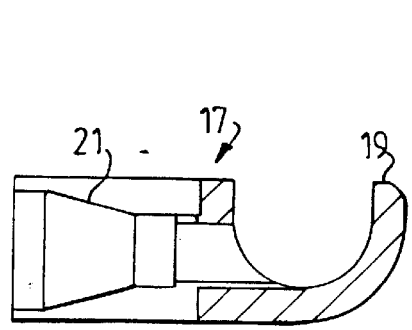
FIG. 11a is a longitudinal sectioned side view of the second implant shown in FIG. 11.
Figure 11:
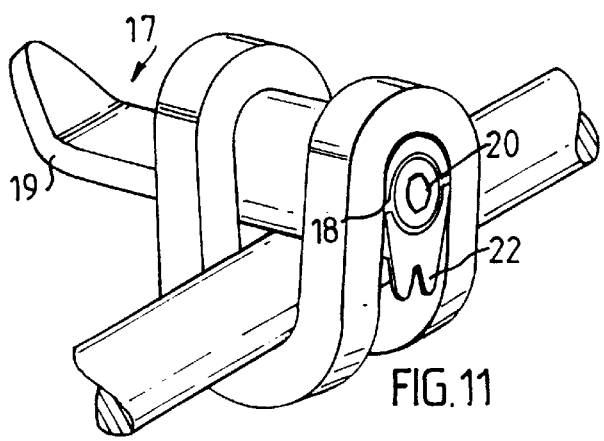
FIG. 11 shows another embodiment of the device with the second implant in the form of an elongated element which is curved at one end and slotted at the other end, this latter end being provided with a bore for receiving a conical screw.
Figure 13:
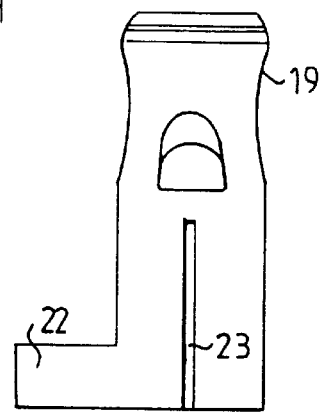
FIG. 13 shows the implant of FIG. 11 from above.
Figure 14:
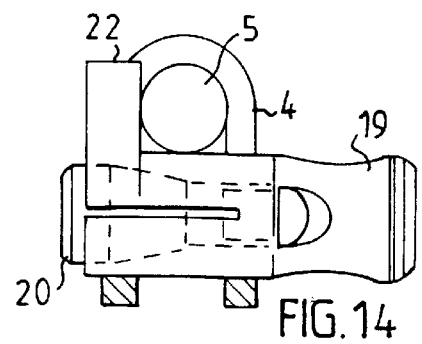
FIG. 14 shows the device of FIG. 8 with a second implant according to FIG. 11 placed at an angle of substantially 90° to the rod-shaped first implant, and comprising an implant locking screw, this view being taken from above.

As will be seen from FIGS. 11 and 14, the hooped holding and clasping part 4 embraces the rod implant element 5 and a hook-shaped member 17 which partially embraces the vertebra and locks the device. The hook-shaped member 17 includes a hollow, straight first end-part 18 having preferably two axially extending slots and a hook-shaped second end-part 19 which is configured substantially to conform to the shape of vertebra curvature and which may either embrace the vertebra cranially or caudally. Extending from the upper hollow end 18 of the hook-shaped member is a lug 22, preferably an arcuate lug, which extends transversely at 90° to the longitudinal axis of the hook-shaped member and which is adapted to fit into the residual space in the hooped part 4. This lug 22 prevents rotation of the cylinder as a conical screw 20 fitted into the upper hollow end 18 of the hook-shaped member is tightened. As the screw 20 is tightened, the cylindrical part widens or expands at this end, therewith firmly clamping a part of the hoop 4 therein. The hook-shaped member 17 is thus firmly clamped between the hooped part 4 and the rod implant 5. With the conical screw 20 loosely tightened in the hook-shaped member 17, the mutually crossing elements in the locking device 1 can be moved relative to one another for adjustment of the positions of the rod 5 and the hook-shaped member 17 in relation to one another and in relation to the vertebrae. The arcuate lug 22 prevents the hook-shaped member being pressed too deeply into the hooped holding and clasping part and when effectively in position in said hooped part, the hook-shaped member cannot be moved further thereinto. Tightening of the conical screw 20 will lock the rod 5 and the hook-shaped member 17 positioned partially around the vertebra against further movement, since the space in the device which accommodates said member and said rod decreases in size and causes the four parts of the device that extend between the rod and the bone screw to stretch. The locking device 1 thus provides a double grip around each of the mutually crossing elements 5, 17, with said elements embraced by the part-hoops 7, 9; 8, 10 around essentially half their circumference and with the mutually parallel, flat side surfaces 13, 14, 13', 14'; 15, 16, 15', 16' that face towards respective elements lying in abutment therewith.

In order to enable the hook-shaped member 17 to be placed beneath and/or over one and the same vertebra, it is necessary to provide the hook-shaped members of different lengths and to place the lug 22 either to the left or to the right of the hook.

A combination of two such members having hooks which embrace a vertebra both at the upper and the lower vertebra arch will provide a strong vertebra securing grip.

It will be understood that the invention is not restricted to the aforedescribed and illustrated embodiments and that modifications can be made within the scope of the following

I claim:

1. A device for fixating and positionally adjusting vertebrae in vertebral surgical operations, comprising two crossing, generally rod-shaped implant elements, and four elongated and generally parallel elements for mutually locking said rod-shaped implant elements together and where said elongated elements are projected on a plane extending through said elongated elements, ends thereof are located generally in the corners of a parallelogram, wherein respective ends are mutually connected in pairs by mutually parallel part-hoops which curve outwards from the ends of the elongated elements, wherein the pair of part-hoops located at one end of the elongated elements are perpendicular to the pair of part-hoops at the other end thereof, wherein each pair of part-hoops embraces a separate one of the two rod-shaped implant elements to provide adjacent, crossing rod-shaped implant elements, and wherein each side of the elongated elements that lies against a rod-shaped implant element is essentially flat and essentially parallel with the respective opposing side of an adjacent elongated element, such as to fixate and positionally adjust a vertebra, and wherein said two rod-shaped implant elements are in direct contact with each other and with said part-hoops in the fixated state of said rod-shaped implant elements, said device also being tightened around said crossing rod-shaped implant elements.

2. A device according to claim 1, wherein one of the rod-shaped implant elements has an expandable part which functions to fixate the two rod-shaped implant elements in relation to one another and said expandable part coacts with a hooped holding and clasping part to obtain an enhanced holding and clasping effect.

3. A device according to claim 1 wherein one of the rod-shaped implant elements is a bone screw having an expandable upper part.

4. A device according to claim 3, wherein the upper part of the bone screw has a hollow interior and a plurality of longitudinally extending slots in communication with said hollow interior.

5. A device according to claim 3, wherein the upper part of the bone screw has a threaded hollow interior and a cylindrical screw for coacting with the threaded hollow interior and having an increasing diameter.

6. A device according to claim 3, wherein the upper part of the bone screw has a conical hollow interior and at least one slot in the longitudinal direction of the bone screw in communication with said hollow interior.

7. A device for fixating and locking two mutually crossing and generally rod-shaped implant elements according to claim 2, characterized in that one (11a) of the implant elements (5, 11a) is a bone screw (11a) having an outer conical upper part (18b) which as it is screwed in causes a reduction in the implant accommodating space in the device (1) and therewith locks the implant (5, 11a) in said device.

8. A device for fixating and locking two mutually crossing and generally rod-shaped implant elements according to claim 2, characterized in that one of the implants (5, 6, 11a, 17) is a hook-shaped member (17) having an expandable first end (18).

9. A device for fixating and locking two mutually crossing and generally rod-shaped implant elements according to claim 8, characterized in that the other end (19) of the hook-shaped member (17) is comprised of a hook-like part intended to partially embrace a vertebra.

10. A device for fixating and locking two mutually crossing and generally rod-shaped implant elements according to claim 8, characterized in that the first end (18) of the hook-shaped member is slotted axially (22) and provided with a screw-thread for coaction with a conical screw (21).

11. A device for fixating and locking two mutually crossing and generally rod-shaped implant elements according to claim 8, characterized in that the first end (18) of the hook-shaped member carries a lug (22) which extends transversely to the longitudinal direction of said member at an angle of 90° thereto and which preferably has an arcuate form and includes gripping grooves (24).

12. A device for fixating and locking two mutually crossing and generally rod-shaped implant elements according to claim 1, characterized in that one of the elongated elements (B, C, D, E) is divided into two parts such as to form two mutually spaced free ends (2, 3), wherein said ends (2, 3) are displaceable relative to one another by means of a displacing and locking means (11), such that the elongated elements will be curved slightly towards one another when locking said displacing and locking means (11) and therewith lock the rod-shaped implant elements (5, 6) together.

13. A device according to claim 12, characterized in that the displacing and locking means (11) is located excentrically to the divided elongated element (B).

14. A device according to claim 12, characterized in that said displacing and locking means (11) is comprised of a screw (12) with coacting screw-thread.

15. A device according to 12, characterized in that one of the elongated elements (E) located nearest the divided element (B) is stiffer than remaining elements, such that said remaining elements will be rotated or twisted slightly as the ends (2, 3) in question are displaced relative to one another such as to enhance locking of the rod-shaped implant elements (5, 6).

* * * * *